(12) United States Patent
Fujiwara et al.

(10) Patent No.: US 7,038,087 B2
(45) Date of Patent: May 2, 2006

(54) PROCESS FOR THE PRODUCTION OF OPTICALLY ACTIVE AMINO ALCOHOLS

(75) Inventors: Takahiro Fujiwara, Hiratsuka (JP); Hideki Nara, Hiratsuka (JP); Tsukasa Sotoguchi, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 159 days.

(21) Appl. No.: 10/656,617

(22) Filed: Sep. 4, 2003

(65) Prior Publication Data

US 2004/0063999 A1 Apr. 1, 2004

(30) Foreign Application Priority Data

Sep. 6, 2002 (JP) ............................. 2002-262019
Jun. 30, 2003 (JP) ............................. 2003-186728

(51) Int. Cl.
*C07C 209/16* (2006.01)
*C07C 209/46* (2006.01)
*C07C 209/56* (2006.01)

(52) U.S. Cl. ...................................... 564/445; 564/462
(58) Field of Classification Search .................... 564/1, 564/123, 148
See application file for complete search history.

(56) References Cited

FOREIGN PATENT DOCUMENTS

| JP | 61-063690 | 4/1986 |
|---|---|---|
| JP | 62-265293 | 11/1987 |
| JP | 04-139140 | 5/1992 |
| JP | 10-182678 | 7/1998 |
| JP | 11-269185 | 10/1999 |
| JP | 2000-016997 | 1/2000 |
| WO | WO 98/54350 | 12/1998 |

OTHER PUBLICATIONS

Bertau et. al., Tetrahedron, Asymmetry, 12, (2001), 2103-2107.*
Ratovelomanana, J. of Org. Chem., 567, (1998), 163-171).*
M. Tichy et al., *Coll. Czechoslov. Chem. Commun.*, vol. 27, pp. 2907-2924, 1962.
E. Smissman et al., *J. Med. Chem.*, vol. 9, pp. 458-465, 1966.
M. Bertau et al., *Tetrahedron Asymmetry*, vol. 12, No. 15, pp. 2103-2107, 2001.
V. Ratovelomanana et al., *Journal of Organ. Chem.*, vol. 567, pp. 163-171, 1998.
Priority Document No. 625679.
Mashima et al., "Synthesis of New Cationis BINAP-Ruthenium (II) Complexes and their Use in Asymmetric Hydrogenation[BINAP=2,2'-bis(diphenylphosphino)-1,1-binaphthyl]", J. Chem. Soc., Chem. Commun, pp. 1208-1210, (1989).
Ami et al., "Lipase-catalyzed Kinetic Resolution of (+)—trans-and cis-2-Azidocycloalkanols". Biosci. Biotechnol. Biochem., 63 (12), pp. 2150-2156, (1999).
Bertau et al., "A Novel Highly Stereoselective Synthesis of Chiral 5- and 4, 5-Substituted 2-Oxazolidinones", Tetrahedron: Asymmetry 12 pp. 2103-2107, (2001).
Overman et al., "A Convenient Method for Obtaining trans-2-Aminocyclohexanol and trnas-2-Aminocyclopentanol in Enantiomerically Pure Form", J. Org. Chem., vol. 50, pp. 4154-4155, (1985).
Coe et al., "Potassium trimethlsilanolate Induced Cleavage of 1,3-oxazolidin-2-and 5-ones, and Application to the Sysnthesis of ®-Salmeterol", Org. Biomol. Chem, vol. 1, pp. 1106-1111, (2003).
Greene et al., "Protective Groups in Organic Sysnthesis", Second Edition, pp. 314-341.

* cited by examiner

*Primary Examiner*—Brian Davis
(74) *Attorney, Agent, or Firm*—Peter F. Corless; Christine C. O'Day; Edwards Angell Palmer & Dodge, LLP

(57) ABSTRACT

An object of the present invention is to provide a process for the production of an optically active amino alcohol, particularly an optically active amino alcohol of a trans-form, being excellent in economy and efficiency, and suitable for industry using easily available and less expensive materials.

The present invention relates to a process for the production of an optically active amino alcohol comprising the steps that an optically active hydroxy ester in a trans-form obtained by an asymmetric hydrogenation of an easily available β-keto ester is reacted with hydrazine, the resulting optically active hydrazinocarbonyl alcohol is subjected to a Curtius rearrangement in the presence of alcohol and protective group of amino group of the resulting optically active alkoxycarbonylamino alcohol is deprotected. As a result of the process for the production in accordance with the present invention, the objected substance is able to be prepared in a high optical purity and in a high yield.

7 Claims, No Drawings

PROCESS FOR THE PRODUCTION OF OPTICALLY ACTIVE AMINO ALCOHOLS

BACKGROUND OF THE INVENTION

1. Field of the Invention

The present invention relates to a process for the production of optically active amino alcohols which are useful as synthetic intermediates, functional materials, etc. for pharmaceuticals, agricultural chemicals, etc.

2. Description of the Related Art

A process for the synthesis of optically active amino alcohols, there have been known, for example, a method where an optically active phenethylamine is added to cyclohexene oxide in the presence of trialkyl aluminum and deprotected (L. E. Overman, et al., J. Org. Chem., 1985, volume 50, pages 4154–4155), a method where an azide is added to cyclohexene oxide, the resulting 2-azidocycloalkanol is subjected to an optical resolution using lipase and the azide is reduced (Ei'ichi Ami, et al.; Biosci. Biotechnol. Biochem., 1999, volume 63, no. 12, pages 2150–2156) and a method where a 2-oxocycloalkanecarboxylate is reduced with baker's yeast, the resulting optically active cis-2-hydroxycycloalkanecarboxylate is led to a hydrazide and reacted with nitrous acid and the resulting oxazolidinone is saponified with an aqueous solution of lithium hydroxide (M. Bertau, et al., Tetrahedron: Asymmetry, 2001, volume 12, pages 2103–2107).

However, the conventional methods are still not suitable for industrial application in view of economy and efficiency, and there has been a demand for the development of an industrially suitable method for the production of optically active amino alcohols.

SUMMARY OF THE INVENTION

An object of the present invention is to provide a process for the production of optically active amino alcohols, particularly optically active amino alcohols of a trans-form, being excellent in economy and efficiency, and suitable for industry using easily available and less expensive materials.

Under such circumstances, the present inventors have carried out intensive studies for achieving the above object. As a result, it has been found that optically active amino alcohols are able to be prepared in a high optical purity and in a high yield when optically active hydroxy esters in a trans-form obtained by an asymmetric hydrogenation of easily available β-ketoesters is reacted with hydrazine, the resulting optically active hydrazinocarbonyl alcohols are subjected to a Curtius rearrangement in the presence of alcohol and the protective group of amino group of the resulting optically active alkoxycarbonylamino alcohols is deprotected whereupon the present invention has been achieved.

Thus, the present invention relates to a process for the production of an optically active amino alcohol represented by the following formula (I)

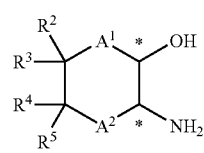

(wherein, $R^2$, $R^3$, $R^4$, $R^5$, $A^1$, $A^2$, m, n and * have the same meanings which will be defined below where the relative configuration of hydroxyl group to amino group on each of asymmetric carbons marked * is trans) or a salt thereof, comprising by reacting an optically active hydroxycarboxylate represented by the following formula (IV)

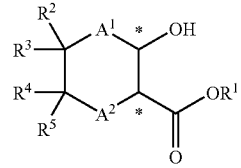

(wherein, $R^1$ is an alkyl group having 1 to 6 carbon(s); $R^2$, $R^3$, $R^4$, and $R^5$ each independently represent hydrogen atom, a lower alkyl group or an optionally-substituted phenyl group; with proviso that $R^2$ and $R^4$ or $R^2$ and $R^5$ or $R^3$ and $R^4$ or $R^3$ and $R^5$ taken together with the carbon atoms to which they are attached optionally form a ring or fused ring; $A^1$ is —(CH$_2$)$_m$— while $A^2$ is —(CH$_2$)$_n$— (where m and n each is an integer of 0 to 3 and m+n is 1 to 3); and * is an asymmetric carbon atom where the relative configuration of hydroxyl group to alkoxycarbonyl group on each of the asymmetric carbons marked * is trans) with hydrazine to prepare an optically-active hydroxycarboxylic hydrazide compound represented by the following formula (III)

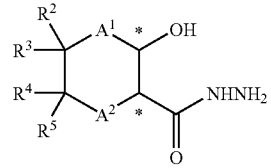

(wherein, $R^2$, $R^3$, $R^4$, $R^5$, $A^1$, $A^2$, m, n and * have the same meanings as defined above where the relative configuration of hydroxyl group to hydrazinocarbonyl group on each of asymmetric carbons marked * is trans), then conducting a Curtius reaction in the presence of an alcohol represented by the following formula (VI)

$$R^6OH \qquad (VI)$$

(wherein, $R^6$ is an alkyl group having 1 to 6 carbon(s) or an optionally-substituted benzyl group) to give an optically active alkoxycarbonylamino alcohol represented by the following formula (II)

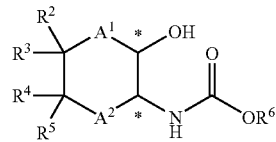

(wherein, $R^2$, $R^3$, $R^4$, $R^5$, $R^6$, $A^1$, $A^2$, m, n and * have the same meanings as defined above where the relative configuration of hydroxyl group to alkoxycarbonylamino group on each of asymmetric carbons marked * is trans) and then deprotected a protective group for the amino group.

The present invention also relates to a process for the production of an optically active alkoxycarbonylamino alcohol represented by the following formula (II)

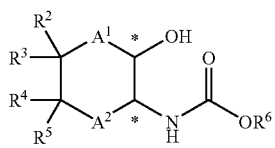

(II)

(wherein, $R^2$, $R^3$, $R^4$, $R^5$, $R^6$, $A^1$, $A^2$, m, n and * have the same meanings as defined above where the relative configuration of hydroxyl group to alkoxycarbonylamino group on each of asymmetric carbons marked * is trans), comprising by reacting an optically active hydroxycarboxylate represented by the following formula (IV)

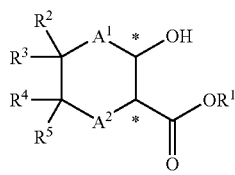

(IV)

(wherein, $R^1$, $R^2$, $R^3$, $R^4$, $R^5$ $A^1$, $A^2$, m, n and * have the same meanings as defined above where the relative configuration of hydroxyl group to alkoxycarbonyl group on each of the asymmetric carbons marked * is trans) with hydrazine to prepare an optically-active hydroxycarboxylic hydrazide compound represented by the following formula (III)

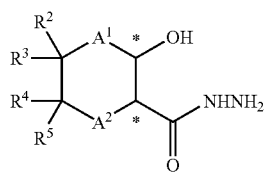

(III)

(wherein, $R^2$, $R^3$, $R^4$, $R^5$, $A^1$, $A^2$, m, n and * have the same meanings as defined above where the relative configuration of hydroxyl group to hydrazinocarbonyl group on each of asymmetric carbons marked * is trans) and conducting a Curtius reaction in the presence of an alcohol represented by the following formula (VI)

$R^6OH$ (VI)

(wherein, $R^6$ has the same meaning as defined above).

DETAILED DESCRIPTION OF THE PREFERRED EMBODIMENTS

The present invention will now be illustrated in detail as hereunder.

The process for the production of the optically active amino alcohols in the present invention will be briefly illustrated by the following reaction scheme.

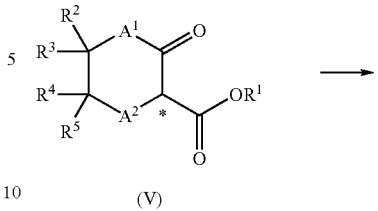

(V)

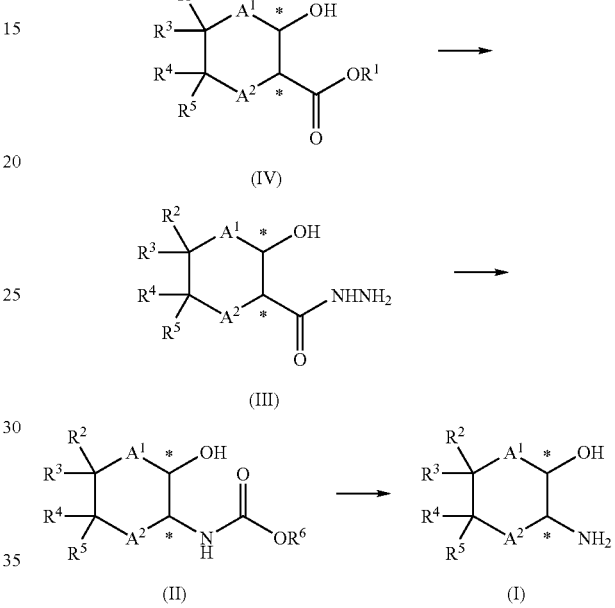

(In the above reaction scheme, $R^1$ is an alkyl group having 1 to 6 carbon(s); $R^2$, $R^3$, $R^4$, and $R^5$ each independently is hydrogen atom, a lower alkyl group or an optionally-substituted phenyl group; with proviso that $R^2$ and $R^4$ or $R^2$ and $R^5$ or $R^3$ and $R^4$ or $R^3$ and $R^5$ taken together with the carbon atoms to which they are attached optionally form a ring or fused ring; $A^1$ is —$(CH_2)_m$— while $A^2$ is —$(CH_2)_n$— (where m and n each is an integer of 0 to 3 and m+n is 1 to 3); and * is an asymmetric carbon atom where the relative configuration of the substituents on each of the asymmetric carbons marked * is trans.)

Thus, an optically active hydroxycarboxylate (IV) is reacted with hydrazine to give an optically active hydroxycarboxylic hydrazide (III), then it is subjected to a Curtius rearrangement in the presence of alcohol to give an optically active alkoxycarbonylamino alcohol (II) and a protective group of the amino group thereof is deprotected to give an optically active cyclic amino alcohol (I). When a necessary amount of acid is existed in the system during the deprotection reaction or during the working up thereof, a salt thereof is produced.

An optically active hydroxycarboxylate (IV) which is the starting material for the process for the production of the present invention may, for example, be manufactured by an asymmetric hydrogenation of a β-keto ester represented by the following formula (V)

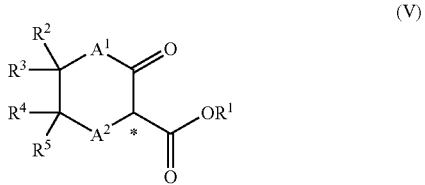

(wherein, $R^1$, $R^2$, $R^3$, $R^4$, $R^5$, $A^1$, $A^2$, m and n have the same meanings as defined above) in the presence of a ruthenium complex where an optically active phosphine compound as a ligand.

An optically active hydroxycarboxylate (IV) which is a starting material of the present invention is a known substance and is able to be prepared by various known method, it is preferred to prepare by an asymmetric hydrogenation of the β-keto ester (V) in the presence of a ruthenium complex including an optically active phosphine compound as a ligand. The reaction is shown below.

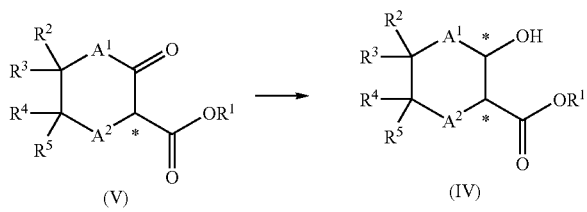

(Wherein, $R^1$, $R^2$, $R^3$, $R^4$, $R^5$, $A^1$, $A^2$, m, n and * have the same meanings as defined above where the relative configuration of hydroxyl group to alkoxycarbonyl group on each of the asymmetric carbons marked * in the formula (IV) is trans.)

The alkyl group represented by $R^1$ in the above formulae (IV) and (V), a straight or branched alkyl group having 1 to 6 carbon(s) is exemplified as a preferred one such as methyl group, ethyl group, n-propyl group, isopropyl group, n-butyl group, isobutyl group, sec-butyl group, tert-butyl group, pentyl group and hexyl group.

The lower alkyl group represented by $R^2$ to $R^5$ in the above formulae (I), (II), (III), (IV) and (V), there may be exemplified a straight or branched alkyl group having 1 to 4 carbon(s) such as methyl group, ethyl group, n-propyl group, isopropyl group, n-butyl group, isobutyl group, sec-butyl group and tert-butyl group.

The substituent for phenyl group which may have substituent represented by $R^2$, $R^3$, $R^4$, and $R^5$, there is no particular limitation so far as it is a group which does not participate in the reaction and there may be exemplified a lower alkyl group such as methyl group, ethyl group, n-propyl group, isopropyl group, n-butyl group, isobutyl group, sec-butyl group and tert-butyl group; a lower alkoxy group such as methoxy group, ethoxy group, propoxy group and isopropoxy group; and halogen atoms such as fluorine atom, chlorine atom and bromine atom.

Any of one to five group(s) as such may be used and, when there are plural groups, it is not necessary that all of them are same.

The ring when $R^2$ and $R^4$ or $R^2$ and $R^5$ or $R^3$ and $R^4$ or $R^3$ and $R^5$ taken together with the carbon atoms to which they are attached optionally form a ring or fused ring, any of aliphatic and aromatic ones may be used. The aliphatic ring, there may be exemplified a polymethylene chain to form a ring having 3 to 6 carbons and its specific examples are trimethylene, tetramethylene, pentamethylene and hexamethylene. Such a group may also have substituent(s) which do(es) not participate in the reaction and specific examples of the substituent(s) as such are a lower alkyl group such as methyl group, ethyl group, n-propyl group, isopropyl group, n-butyl group, isobutyl group, sec-butyl group and tert-butyl group; a lower alkoxy group such as methoxy group, ethoxy group, propoxy group and isopropoxy group; and halogen atoms such as fluorine atom, chlorine atom and bromine atom.

Specific examples of an aromatic ring where $R^2$ and $R^4$ or $R^2$ and $R^5$ or $R^3$ and $R^4$ or $R^3$ and $R^5$ taken together with the carbon atoms to which they are attached optionally form a ring or fused ring are benzene ring, naphthalene ring, phenanthrene ring, furan ring, thiophene ring, benzofuran ring, isobenzofuran ring, pyrrole ring, pyridine ring, pyrimidine ring, pyridazine ring, indole ring, isoindole ring, quinoline ring and isoquinoline ring. The aromatic ring as such may have substituent(s) which do(es) not participate in the reaction and specific examples of the substituent(s) as such are a lower alkyl group such as methyl group, ethyl group, n-propyl group, isopropyl group, n-butyl group, isobutyl group, sec-butyl group and tert-butyl group; a lower alkoxy group such as methoxy group, ethoxy group, propoxy group and isopropoxy group; and halogen atom such as fluorine atom, chlorine atom and bromine atom.

An alkyl group represented by $R^6$ in the above formulae (II) and (VI), there may be exemplified an alkyl group having 1 to 4 carbon(s) such as methyl group, ethyl group, n-propyl group, isopropyl group, n-butyl group, isobutyl group, sec-butyl group and tert-butyl group.

The optionally substituted benzyl group, there may be exemplified benzyl group which may have one or more substituent(s). The substituent for benzyl group, there is no particular limitation so far as it does not participate in the reaction and there may be exemplified an alkyl group such as methyl group, ethyl group, n-propyl group, isopropyl group, n-butyl group, isobutyl group, sec-butyl group and tert-butyl group; an alkoxy group such as methoxy group, ethoxy group, propoxy group and isopropoxy group; halogen atom such as fluorine atom, chlorine atom and bromine atom; nitro group; and phenyl group. The position to be substituted, it may be of any position of benzene ring and methylene group.

When $R^6$ is an optionally substituted benzyl group, its specific examples are benzyl group, p-methylphenylmethyl group, p-ethylphenylmethyl group, p-methoxyphenylmethyl group, 3,5-dimethylphenylmethyl group, p-fluorophenylmethyl group, p-chlorophenylmethyl group, 2,6-dichlorophenylmethyl group, α-phenylethyl group, o-nitrophenylmethyl group, p-nitrophenylmethyl group, p-cyanophenylmethyl group, diphenylmethyl group, triphenylmethyl group, naphthylmethyl group, naphthyldiphenylmethyl group and p-methoxyphenyldiphenylmethyl group. More preferred examples are benzyl group, p-methylphenylmethyl group, p-ethylphenylmethyl group, p-methoxyphenylmethyl group, 3,5-dimethylphenylmethyl group, 3,5-dimethoxyphenylmethyl group, p-fluorophenylmethyl group, p-chlorophenylmethyl group and α-phenylethyl group. Still more preferred example is benzyl group.

In the formulae (I) to (V), $A^1$ is $—(CH_2)_m—$, $A^2$ is $—(CH_2)_n—$ and m and n each is an integer of 0 to 3 where, when m is 0, then $A^1$ is a single bond (a linkage) while, when n is 0, then $A^2$ is a single bond (a linkage).

The β-keto ester represented by the formula (V), there is no particular limitation so far as it is a compound having a five- to seven-membered carbon ring, having (substituted) alkoxycarbonyl group and β-oxo group and having no functional group which is reactive under the reaction condition for the reduction reaction of oxo group. Specific examples of the β-keto ester as such are methyl 2-oxocyclopentanecarboxylate, ethyl 2-oxocyclopentanecarboxylate, butyl 2-oxocyclopentanecarboxylate, hexyl 2-oxocyclopentanecarboxylate, methyl 3,4-dimethyl-2-oxocyclopentanecarboxylate, methyl 3-ethyl-2-oxocyclopentanecarboxylate, ethyl 3,4-dibutyl-2-oxocyclopentanecarboxylate, methyl 3,4,4-trimethyl-2-oxocyclopentanecarboxylate, methyl 3-phenyl-2-oxocyclopentanecarboxylate, methyl 3,4-diphenyl-2-oxocyclopentanecarboxylate, butyl 3-(p-tolyl)-2-oxocyclopentanecarboxylate, methyl 3-(o-tolyl)-2-oxocyclopentanecarboxylate, methyl 3-(4-methoxyphenyl)-2-oxocyclopentanecarboxylate, methyl 3-(4-n-butoxyphenyl)-2-oxocyclopentanecarboxylate, methyl 3,4-di(4-fluorophenyl)-2-oxocyclopentanecarboxylate, methyl 3-(4-chlorophenyl)-2-oxocyclopentanecarboxylate, methyl 1-oxo-2-indanecarboxylate, methyl 5-methyl-1-oxo-2-indanecarboxylate, methyl 6-fluoro-1-oxo-2-indanecarboxylate, methyl 1-oxo-2-perhydroindanecarboxylate, methyl 5-methoxy-1-oxo-2-perhydroindanecarboxylate, methyl 2-oxocyclohexanecarboxylate, ethyl 2-oxocyclohexanecarboxylate, hexyl 2-oxocyclohexanecarboxylate, ethyl 3-methyl-2-oxocyclohexanecarboxylate, ethyl 3-butyl-4-methyl-2-oxocyclohexanecarboxylate, ethyl, 3,4,4-trimethyl-2-oxocyclohexanecarboxylate, ethyl 4-(tert-butyl)-2-oxocyclohexanecarboxylate, hexyl 3,4-diphenyl-2-oxocyclohexanecarboxylate, methyl 3-(4-isopropoxyphenyl)-2-oxocyclohexanecarboxylate, methyl 4-(2-fluorophenyl)-2-oxocyclohexanecarboxylate, ethyl 1-oxo-1,2,3,4-tetrahydronaphthalene-2-carboxylate, ethyl 6-methoxy-1-oxo-1,2,3,4-tetrahydronaphthalenecarboxylate, methyl 1-oxoperhydronaphthalenecarboxylate, methyl 6-flouoro-1-oxoperhydronaphthalenecarboxylate, methyl 2-oxocycloheptanecarboxylate, ethyl 2-oxocycloheptanecarboxylate, butyl 2-oxocycloheptanecarboxylate, ethyl 3-methyl-2-oxocycloheptanecarboxylate, ethyl 3-butyl-4-methyl-2-oxocycloheptanecarboxylate, ethyl 3-phenyl-2-oxocycloheptanecarboxylate, methyl 2-oxoindanecarboxylate, methyl 5-methyl-2-oxoindanecarboxylate, methyl 6-fluoro-2-oxoindanecarboxylate, methyl 5-methyl-2-oxoindanecarboxylate, methyl 2-oxoperhydroindanecarboxylate, methyl 5-methoxy-2-oxohydroindanecarboxylate, ethyl 2-oxo-1,2,3,4-tetrahydronaphthalenecarboxylate, ethyl 3-oxo-1,2,3,4-tetrahydronaphthalenecarboxylate, ethyl 6-methoxy-2-oxo-1,2,3,4-tetrahydronaphthalenecarboxylate, methyl 2-oxoperhydronaphthalenecarboxylate, methyl 3-oxoperhydronaphthalene-2-carboxylate, methyl 6-fluoro-2-oxoperhydronaphthalenecarboxylate and methyl 1-oxoperhydroazulene-2-carboxylate.

A preferred embodiment of the process for the production according to the present invention, there may be exemplified a method where a β-keto ester represented by the formula (V) is subjected to an asymmetric hydrogenation in the presence of a ruthenium complex including an optically active phosphine compound as a ligand to give an optically active hydroxycarboxylate represented by the formula (IV).

The optically active phosphine compound used for the asymmetric hydrogenation, there may be exemplified an optically active phosphine compound represented by the following formula (VII)

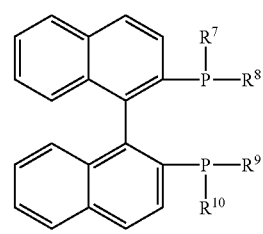

(VII)

(wherein, $R^7$, $R^8$, $R^9$ and $R^{10}$ each independently is an optionally substituted aryl group or an optionally substituted cycloalkyl group having 3 to 8 carbons).

An aryl group for the optionally-substituted aryl group represented by $R^7$, $R^8$, $R^9$ and $R^{10}$ in the above formula (VII), its preferred examples are phenyl group and naphthyl group. Specific examples of the cycloalkyl group having 3 to 8 carbons are cyclopropyl group, cyclopentyl group, cyclohexyl group, cycloheptyl group and cyclooctyl group.

Examples of the substituent for those aryl group and cycloalkyl group are an alkyl group having 1 to 4 carbon(s) such as methyl group, ethyl group, n-propyl group, isopropyl group, n-butyl group, isobutyl group, sec-butyl group and tert-butyl group; halogen atom such as fluorine atom, chlorine atom and bromine atom; an alkoxy group having 1 to 4 carbon(s) such as methoxy group, ethoxy group, propoxy group and butoxy group; a halogenated alkyl group such as trifluoromethyl group and trichloromethyl group; and benzyloxy group.

Specific examples of the preferred $R^7$, $R^8$, $R^9$ and $R^{10}$ are phenyl group, 4-tolyl group, 3-tolyl group, 4-methoxyphenyl group, 3,5-xylyl group, 3,5-di-tert-butylphenyl group, 4-methoxy-3,5-dimethylphenyl group, 4-methoxy-3,5-di-tert-butylphenyl group, naphthyl group, cyclopentyl group and cyclohexyl group.

Specific examples of the preferred optically active phosphine compound represented by the above formula (VII) are the tertiary phosphine compounds described, for example, in JP-A-61-63690 and JP-A-62-265293. Preferred specific examples as such are listed as follows.

2,2'-Bis(diphenylphosphino)-1,1'-binaphthyl, 2,2'-bis[di(p-tolyl)phosphino]-1,1'-binaphthyl, 2,2'-bis[di(3,5-xylyl)phosphino]-1,1'-binaphthyl, 2,2'-bis[di-(3,5-di-tert-butyl)phosphino]-1,1'-binaphthyl, 2,2'-bis[di-(4-methoxy-3,5-dimethylphenyl)phosphino]-1,1'-binaphthyl, 2,2'-bis(dicyclopentylphosphino)-1,1'-binaphthyl and 2,2'-bis(dicyclohexylphosphino)-1,1'-binaphthyl.

Another optically active phosphine compound used for the asymmetric hydrogenation according to the present invention, there maybe exemplified an optically active phosphine compound represented by the following formula (VIII)

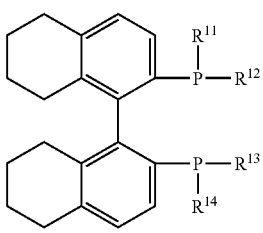

(VIII)

(wherein, $R^{11}$, $R^{12}$, $R^{13}$ and $R^{14}$ each independently is an optionally substituted aryl group or an optionally substituted cycloalkyl group having 3 to 8 carbons).

In the above formula (VIII), specific examples of the optionally substituted aryl group or the optionally substituted cycloalkyl group having 3 to 8 carbons represented by $R^{11}$, $R^{12}$, $R^{13}$ and $R^{14}$ are the same as those for $R^7$, $R^8$, $R^9$ and $R^{10}$.

The preferred specific examples of the optically active phosphine compound represented by the above formula (VIII), there may be exemplified the tertiary phosphine compounds mentioned in JP-A-04-139140. The preferred specific examples as such are listed below.

2,2'-Bis(diphenylphosphino)-5,5',6,6',7,7',8,8'-octa-hydro-1,1'-binaphthyl, 2,2'-bis[di(p-tolyl)phosphino]-5,5',6,6', 7,7',8,8'-octahydro-1,1'-binaphthyl, 2,2'-bis[di(3,5-xylyl)phosphino]-5,5',6,6',7,7',8,8'-octahydro-1,1'-binaphthyl and 2,2'-bis[di(4-methoxy-3,5-dimethylphenyl)phosphino]-5,5', 6,6',7,7',8,8'-octahydro-1,1'-binaphthyl.

Another optically active phosphine compound used for the asymmetric hydrogenation of the present invention, there may be exemplified an optically active phosphine compound represented by the following formula (IX).

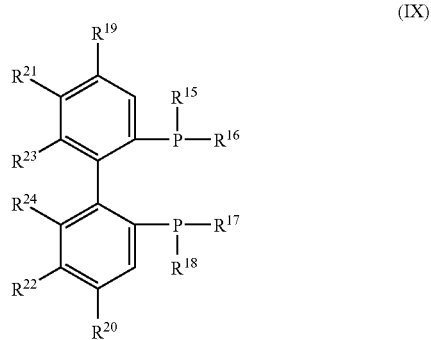

(IX)

(Wherein, $R^{15}$, $R^{16}$, $R^{17}$ and $R^{18}$ each independently is an optionally substituted aryl group or an optionally substituted cycloalkyl group having 3 to 8 carbons; $R^{19}$ and $R^{20}$ each independently is hydrogen atom or an alkyl group having 1 to 4 carbon(s); $R^{21}$ and $R^{22}$ each independently is hydrogen atom, methyl group, methoxy group or halogen atom; $R^{23}$ and $R^{24}$ each independently is methyl group, methoxy group or trifluoromethyl group; and $R^{21}$ and $R^{23}$ or $R^{22}$ and $R^{24}$ taken together may form methylenedioxy group)

Specific examples of the optionally substituted aryl group and the optionally substituted cycloalkyl group having 3 to 8 carbons represented by $R^{15}$, $R^{16}$, $R^{17}$ and $R^{18}$ in the above formula (IX) are the same as those for the above $R^7$, $R^8$, $R^9$ and $R^{10}$.

The preferred specific examples of the optically active phosphine compound represented by the above formula (IX), there may be exemplified the tertiary phosphine compounds mentioned in JP-A-10-182678, JP-A-11-269185, JP-A-2000-16997, etc. The preferred specific examples as such are listed below.

[(5,6),(5',6')-Bis(methylenedioxy)biphenyl-2,2'-diyl]bis (diphenylphosphine), [(5,6),(5',6')-bis(methylenedioxy)biphenyl-2,2'-diyl]bis[di(p-tolyl)phosphine], [(5,6),(5',6')-bis (methylenedioxy)biphenyl-2,2'-diyl]bis[di(3,5-xylyl) phosphine], [(5,6),(5',6')-bis(methylenedioxy)biphenyl-2,2'-diyl] bis[di(4-methoxy-3,5-dimethylphenyl)phosphine], [(5, 6),(5',6')-bis(methylenedioxy)biphenyl-2,2'-diyl]bis[di(4-methoxy-3,5-di-tert-butylphenyl)phosphine] and [(5,6),(5', 6')-bis(methylenedioxy)biphenyl-2,2'-diyl]bis (dicyclohexylphosphine).

Besides the above, the following compounds may be listed as the compound which corresponds to the optically active phosphine compound represented by the formula (IX).

2,2'-Dimethyl-6,6'-bis(diphenylphosphino)-1,1'-biphenyl, 2,2'-dimethyl-6,6'-bis(di(p-tolyl)phosphino)-1,1'-biphenyl, 2,2'-dimethyl-6,6'-bis(di(3,5-xylyl)-phosphino)-1,1'-biphenyl, 2,2'-dimethyl-6,6'-bis(di(4-methoxy-3,5-dimethylphenyl)phosphino)-1,1'-biphenyl, 2,2'-dimethyl-6,6'-bis(di(4-methoxy-3,5-di-tert-butylphenyl)phosphino-1,1'-biphenyl, 2,2'-dimethyl-6,6'-bis-(dicyclohexylphosphino)-1,1'-biphenyl, 2,2'-dimethoxy-6,6'-bis(di(p-tolyl)phosphino)-1,1'-biphenyl, 2,2'-dimethoxy-6,6'-bis(di(3,5-xylyl)phosphino)-1, 1'-biphenyl, 2,2,-dimethoxy-6,6'-bis(di(4-methoxy-3,5-dimethylphenyl)-phosphino)-1,1'-biphenyl, 2,2'-dimethoxy-6,6'-bis(di(4-methoxy-3,5-di-tert-butylphenyl)phosphino)-1,1'-biphenyl, 2,2'-dimethoxy-6,6'-bis (dicyclohexylphosphino)-1,1'-biphenyl, 2,2'-dimethyl-3,3'-dichloro-4,4'-dimethyl-6,6'-bis(diphenylphosphino)-1,1'-biphenyl, 2,2'-dimethyl-3,3'-dichloro- 4,4'-dimethyl-6,6'-bis (di(p-tolyl)phosphino)-1,1'-biphenyl, 2,2'-dimethyl-3,3'-dichloro-4,4'-dimethyl-6,6'-bis(di(3,5-xylyl)phosphino)-1, 1'-biphenyl and 2,2'-dimethyl-3,3'-dichloro-4,4'-dimethyl-6, 6'-bis(di(4-methoxy-3,5-dimethylphenyl)phosphino)-1,1'-biphenyl.

In a preferred process for producing the optically active hydroxycarboxylate represented by the formula (IV) according to the present invention, the β-keto ester represented by the formula (V) is subjected to an asymmetric hydrogenation using a complex comprising one or more of the optically active phosphine compound(s) represented by the above formula (VII), (VIII) or (IX) and ruthenium.

In all of such optically active phosphine compounds, there are (R)-form and (S)-form and, therefore, either of them may be selected depending upon the absolute configuration of the objected optically active hydroxycarboxylate (IV).

A method for the manufacture of the ruthenium complex used in the asymmetric hydrogenation, it can be prepared, for example, according to a method described in the document (K. Mashima, et al., *J. Chem. Soc., Chem. Commun.*, 1208 (1989)) by heating under stirring [Ru(aryl)X$_2$]$_2$ (X is chlorine atom, bromine atom or iodine atom) with L (L is the above-mentioned optically active phosphine compound) in an organic solvent (such as a mixed solvent of methylene chloride and ethanol).

Specific examples of the ruthenium complex prepared as such are the following substances.
[RuCl(benzene)(L)]Cl,
[RuBr(benzene)(L)]Br,
[RuI(benzene)(L)]I,
[RuCl(p-cymene)(L)]Cl,
[RuBr(p-cymene)(L)]Br,
[RuI(p-cymene)(L)]I,
[RuCl(mesitylene)(L)]Cl,
[RuBr(mesitylene)(L)]Br,
[RuI(mesitylene)(L)]I,
[RuCl(hexamethylbenzene)(L)]Cl,
[RuBr(hexamethylbenzene)(L)]Br,
[RuI(hexamethylbenzene)(L)]I,
[{RuCl(L)}$_2$(μ-Cl)$_3$][NH$_2$Me$_2$],
[{RuCl(L)}$_2$(μ-Cl)$_3$][NH$_2$Et$_2$],
[{RuCl(L)}$_2$(μ-Cl)$_3$][NH$_2$Pr$_2$] and
[{RuCl(L)}$_2$(μ-Cl)$_3$][NH$_2$(i-Pr)$_2$].

More preferred examples of the ruthenium complex where the optically active phosphine compound as a ligand used in a preferred process for producing the optically active hydroxycarboxylate represented by the formula (IV) in the present invention are as mentioned below where [(5,6),(5',6')-bis(methylenedioxy)biphenyl-2,2'-diyl]bis(diphenylphosphine) compounds (SEGPHOS compounds; hereinafter, may be abbreviated as "SEGPHOSs") are used as the optically active phosphine compound.

[RuCl(benzene){(R) or (S)-SEGPHOS}]Cl,
[RuBr(benzene){(R) or (S)-SEGPHOS}]Br,
[RuI(benzene){(R) or (S)-SEGPHOS}]I,
[RuCl(p-cymene){(R) or (S)-SEGPHOS}]Cl,
[RuBr(p-cymene){(R) or (S)-SEGPHOS}]Br,
[RuI(p-cymene){(R) or (S)-SEGPHOS}]I,
[RuCl(mesitylene){(R) or (S)-SEGPHOS}]Cl,
[RuBr(mesitylene){(R) or (S)-SEGPHOS}]Br,
[RuI(mesitylene){(R) or (S)-SEGPHOS}]I,
[RuCl(hexamethylbenzene){(R) or (S)-SEGPHOS}]Cl,
[RuBr(hexamethylbenzene){(R) or (S)-SEGPHOS}]Br,
[RuI(hexamethylbenzene){(R) or (S)-SEGPHOS}]I,
[{RuCl[(R) or (S)-SEGPHOS]}$_2$(μ-Cl)$_3$][NH$_2$Me$_2$],
[{RuCl[(R) or (S)-SEGPHOS]}$_2$(μ-Cl)$_3$][NH$_2$Et$_2$],
[{RuCl[(R) or (S)-SEGPHOS]}$_2$(μ-Cl)$_3$][NH$_2$Pr$_2$] and
[{RuCl[(R) or (S)-SEGPHOS]}$_2$(μ-Cl)$_3$][NH$_2$(i-Pr)$_2$].

In order to carry out the asymmetric hydrogenation reaction according to the present invention, it is conducted by subjecting the β-keto ester represented by the formula (V) to an asymmetric hydrogenation reaction in the presence of a ruthenium complex including an optically active phosphine compound as a ligand.

The asymmetric hydrogenation reaction of the present invention may be carried out in an organic solvent. The organic solvent, although there is no particular limitation so far as it does not participate in the reaction, there may be exemplified aromatic hydrocarbons such as toluene, benzene, xylene and chlorobenzene; aliphatic esters such as methyl acetate, ethyl acetate, propyl acetate and butyl acetate; ethers such as diethyl ether, diisopropyl ether and tetrahydrofuran; halogenated hydrocarbons such as dichloromethane, 1,2-dichloroethane and dibromomethane; and alcohols such as methanol, ethanol and isopropanol. Each them may be used solely or two or more may be used as a mixed solvent. Among those solvents, more preferred solvents are alcohols and methanol and ethanol are particularly preferred.

The amount of the solvent used to the material compound (substrate) is within a range of about 0.1- to 10-fold by volume or, preferably, about 0.5- to 3-fold by volume.

Amount of the ruthenium complex used for the asymmetric hydrogenation reaction used in the present invention to 1 mol of the material compound (substrate) is within a range of about 1/20,000 to 1/10 mol or, preferably, about 1/1000 to 1/100 mol.

Pressure of hydrogen is within a range of about 0.5 to 10 MPa or, preferably, about 1 to 5 MPa.

The reaction temperature, a range of about 30 to 100° C. or, preferably, about 50 to 90° C. is adopted and, when the reaction is carried out for about 0.5 to 100 hour(s) or, preferably, about 1 to 24 hour(s) keeping at the above temperature, the asymmetric hydrogenation is able to be smoothly carried out.

The compound represented by the formula (IV) can be prepared from the reaction solution obtained by the above reaction by means of known methods such as extraction with solvent, distillation, crystallization, recrystallization and column chromatography.

The process for producing the optically active hydroxycarboxylic acid hydrazide represented by the formula (III) of the present invention is carried out by the reaction of the optically active hydroxycarboxylate or, preferably, the optically active hydroxycarboxylate represented by the formula (IV) prepared by the above-mentioned method with hydrazine or a hydrate thereof in an organic solvent. The reaction formula is as follows.

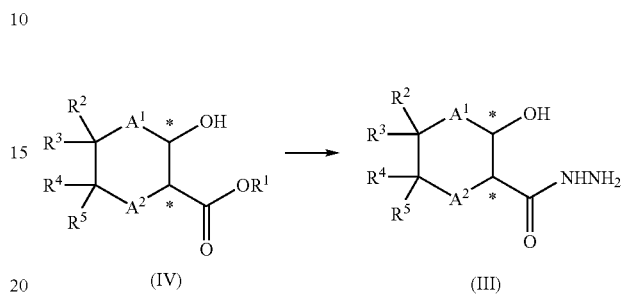

(Wherein, R$^1$, R$^2$, R$^3$, R$^4$, R$^5$, A$^1$, A$^2$, m, n and * have the same meanings as defined above where the relative configuration of hydroxyl group to alkoxycarbonyl group and that of hydroxyl group to hydrazinocarbonyl group on each of asymmetric carbons marked * are trans).

An organic solvent used in the present reaction, although there is no particular limitation as far as it does not participate in the reaction, there may be exemplified aromatic hydrocarbons such as toluene, benzene, xylene and chlorobenzene; ethers such as diethyl ether, diisopropyl ether and tetrahydrofuran; halogenated hydrocarbons such as dichloromethane, 1,2-dichloroethane and dibromomethane; and alcohols such as methanol, ethanol and isopropanol. Each them may be used solely or two or more may be used as a mixed solvent. Among those solvents, more preferred solvents are alcohols and methanol and ethanol are particularly preferred.

Amount of the solvent to the optically active hydroxycarboxylate represented by the formula (IV) which is a substrate is within a range of about 0.1- to 10-fold by volume or, preferably, about 0.5- to 3-fold by volume.

Amount of hydrazine or hydrazine hydrate used in the present reaction to 1 mol of the substrate is within a range of about 1 to 5 mol or, preferably, about 1.1 to 1.5 mol.

The reaction temperature, the range of about 0 to 120° C. is generally adopted and, preferably, that of about 50 to 100° C. is adopted.

The compound represented by the formula (III) can be prepared from the reaction solution obtained by the above reaction by means of known methods such as extraction with solvent, distillation, crystallization, recrystallization and column chromatography.

A process for producing the optically active alkoxycarbonylamino alcohol (II) according to the present invention, it is produced by subjecting the optically active hydroxycarboxylic hydrazide represented by the formula (III) to a Curtius rearrangement reaction in the presence of an alcohol. The reaction formula is as follows.

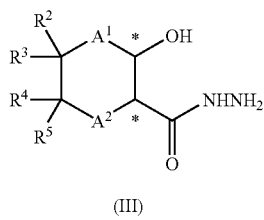

(III)

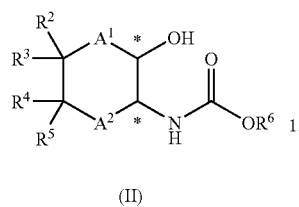

(II)

(Wherein, $R^2$, $R^3$, $R^4$, $R^5$, $R^6$ $A^1$, $A^2$, m, n and * have the same meanings as defined above where the relative configuration of hydroxyl group to hydrazinocarbonyl group and that of hydroxyl group to alkoxycarbonylamino group on each of asymmetric carbons marked * are trans).

In order to carry out the above rearrangement reaction according to the present invention, it is conducted by the reaction of the optically active hydroxycarboxylic hydrazide represented by the formula (III) with a nitrite in an organic solvent in the presence of an alcohol or with a nitrite followed by subjecting to a reaction with an alcohol.

With regard to the alcohol used in the present invention, an alcohol represented by the following formula (VI)

$$R^6OH \quad (VI)$$

(in the formula, $R^6$ has the same meaning as defined above) is listed.

Specific examples of the alcohol represented by the formula (VI) used in the present reaction are aliphatic alcohols such as methanol, ethanol, n-propanol, isopropanol, n-butanol, isobutanol, sec-butanol and tert-butanol; and benzyl alcohols such as benzyl alcohol, p-methylphenyl methanol, p-ethylphenyl methanol, p-methoxyphenyl methanol, 3,5-dimethylphenyl methanol, p-fluorophenyl methanol, p-chlorophenyol methanol, 2,6-dichlorophenyl methanol, α-methylbenzyl alcohol, o-nitrophenyl methanol, p-nitrophenyl methanol, p-cyanophenyl methanol, diphenyl methanol, triphenyl methanol, naphthyl methanol, naphthyldiphenyl methanol and p-methoxyphenyl diphenyl methanol.

More preferred specific examples are benzyl alcohol, p-methylphenyl methanol, p-ethylphenyl methanol, p-methoxyphenyl methanol, 3,5-dimethylphenyl methanol, 3,5-dimethoxyphenyl methanol, p-fluorophenyl methanol, p-chlorophenyl methanol and α-methylbenzyl alcohol. Still more preferred examples are benzyl alcohol, p-methylphenyl methanol, p-methoxyphenyl methanol and α-methylbenzyl alcohol.

Amount of the alcohol used to 1 mol of the compound represented by the formula (III) is not less than 1 mol or, preferably, within a range of 2 to 3 mol.

Specific examples of the nitrite used in the present reaction are sodium nitrite and potassium nitrite.

Amount of the nitrite used to 1 mol of the compound represented by the formula (III) (substrate) is within a range of 1 to 2 mol or, preferably, 1.1 to 1.5 mol.

It is preferred that the rearrangement reaction according to the present invention is carried out in the presence of an acid.

The acid used in the rearrangement reaction, there may be exemplified hydrochloric acid, sulfuric acid, phosphoric acid, acetic acid, methanesulfonic acid, benzenesulfonic acid, p-toluenesulfonic acid and camphorsulfonic acid. Preferred examples are hydrochloric acid, sulfuric acid and acetic acid.

The reaction may be carried out in an organic solvent. The organic solvent, although there is no particular limitation so far as it does not participate in the reaction, there may be exemplified aliphatic hydrocarbons such as hexane and heptane; aromatic hydrocarbons such as toluene, benzene, xylene and chlorobenzene; aliphatic esters such as methyl acetate, ethyl acetate, propyl acetate and butyl acetate; ethers such as diethyl ether, diisopropyl ether and tetrahydrofuran; halogenated hydrocarbons such as dichloromethane, 1,2-dichloroethane, dibromomethane and chloroform; and ketones such as acetone, methyl ethyl ketone, diethyl ketone, methyl isobutyl ketone and cyclohexanone.

Each of them may be used solely or two or more may be used as a mixed solvent. With regard to the solvent, aromatic hydrocarbons may be preferably exemplified and toluene may be more preferably exemplified.

Amount of the solvent used to the substrate is within a range of about 0.1- to 10-fold by volume or, preferably, about 0.5- to 3-fold by volume.

The reaction temperature, a range of about –20 to 100° C. is generally adopted and, preferably, that of about –10 to 60° C. is adopted.

The compound represented by the formula (II) can be prepared from the reaction solution obtained by the above reaction by means of known methods such as extraction with solvent, distillation, crystallization, recrystallization and column chromatography.

Incidentally, according to the process of the present invention, it is possible to prepare the optically active compound (II) where the configuration of the starting compound (III) is retained.

The process for producing the optically active amino alcohol of the present invention (I) or a salt thereof may be carried out by deprotection of the alkoxycarbonyl group which is a protective group on nitrogen atom of the optically active alkoxycarbonylamino alcohol represented by the formula (II). The reaction formula is as follows.

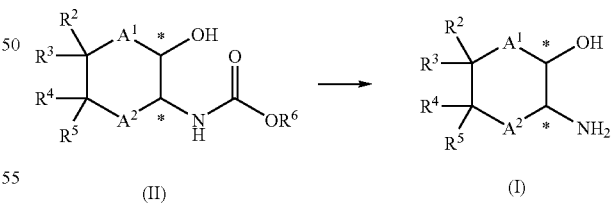

(II)                    (I)

(Wherein, $R^2$, $R^3$, $R^4$, $R^5$, $R^6$, $A^1$, $A^2$, m, n and * have the same meanings as defined above where the relative configuration of hydroxyl group to alkoxycarbonylamino group and that of hydroxyl group to amino group on each of asymmetric carbons marked * are trans).

In order to carry out the deprotection reaction of the present invention, the optically active alkoxycarbonylamino alcohol represented by the formula (II) is subjected, for example, to a method described in Protective Groups in Organic Synthesis, Second Edition, pages 315 to 341, "6. Protection for the Amino Group, Carbamates". Thus, when $R^6$ is an alkyl group such as methyl group or ethyl group, the deprotection may be carried out using an acidic catalyst such as hydrogen bromide/acetic acid or an alkaline catalyst such as potassium hydroxide/water/alcohol. When it is an optionally substituted benzyl group, the deprotection may be carried out by hydrogen gas or the like using a catalyst such as palladium-carbon.

As another method for the deprotection, it is also possible to deprotect using alkaline metal compound of trimethylsilanol such as potassium trimethylsilanolate as described in *Org. Biomol. Chem.*, 2003, 1, 1106–1111.

Thus, resulted the optically active amino alcohol prepared as such may be also obtained as an amine salt using an acid. In order to give an amine salt, the resulting optically active amino alcohol is made to react with a desired acid and, when the deprotection reaction is carried out using excessive acid (amount which is sufficient for forming an amine salt) in case the deprotection is conducted using an acid catalyst, the optically active amino alcohol is obtained as a salt and, therefore, it is also possible to prepare an amine salt by such a method. The resulting amine salt is able to be isolated by a conventional method such as crystallization, recrystallization or concentration of the solvent.

EXAMPLES

The present invention will now be more specifically illustrated by way of the following Examples although the present invention is not limited by those Examples at all.

Incidentally, instruments or apparatuses used for the measurement of the products in the Examples are as follows.

Nuclear magnetic resonance spectrum:
(1) DRX 500 (Bruker Japan Co., Ltd.)
$^1$H-NMR (500 MHz), $^{13}$C-NMR
(2) Gemini 2000 (Varian)
$^1$H-NMR (200 MHz)
Gas chromatography (GLC):
Hewlett Packard 5890-II

Example 1

Synthesis of Methyl (R,R)-2-hydroxycyclopentanecarboxylate

To a one-liter autoclave was added 0.419 g (0.509 mmol) of [Me$_2$NH$_2$][{RuCl ((R)-segphos)}(μ-Cl)$_3$], then a solution containing 72.41 g (509.3 mmol) of methyl 2-oxocyclopentanecarboxylate, 253 mL of methylene chloride and 36 mL of methanol was added and the mixture was stirred at 40° C. for 18 hours under 1 MPa of hydrogen pressure. After cooling, hydrogen was discharged, the solvent was recovered and the residue (100.3 g) was distilled under reduced pressure (70 to 80° C./93.3 Pa) to give 71.15 g of the title compound. The yield was 88%. Enantiomer excessive rate (hereinafter, referred to as "% ee") and diastereomer excessive rate (hereinafter, referred to as "% de") of this compound were analyzed by gas chromatography (column: Chirasil DEX-CB) and found to be 99.3% ee and 96.7% de, respectively.

$^1$H-NMR (500 MHz) δ (CDCl$_3$): 1.6–1.8 (m, 4H), 2.0 (m, 2H), 2.7 (br, 2H), 3.7 (s, 3H), 4.4 (m, 1H).

Example 2

Synthesis of Methyl (S,S)-2-hydroxycyclopentanecarboxylate

To a 100-ml autoclave were added 96.9 mg (0.106 mmol) of [{RuCl(p-cymene)(S)-segphos}]Cl, then a mixed liquid comprising 3.00 g (21.1 mmol) of degassed methyl 2-oxocyclopentanecarboxylate, 15.7 mL of methylene chloride and 2.3 mL of methanol was added and the mixture was stirred at 60° C. for 18 hours under 5 MPa of hydrogen pressure. After cooling, hydrogen was discharged, the solvent was recovered and the residue (3.05 g) was distilled using a Kugelrohr (93.9 Pa) to give 2.33 g of the title compound. The yield was 73%. The resulting product was analyzed and measured by the same manner as in Example 1 whereupon the results were 99.3% ee and 94.2% de.

$^1$H-NMR (200 MHz) δ (CDCl$_3$): 1.6–1.8 (m, 4H), 2.0 (m, 2H), 2.7 (br, 2H), 3.7 (s, 3H), 4.4 (m, 1H).

Example 3

Synthesis of Ethyl (R,R)-2-hydroxycyclohexanecarboxylate

To a one-liter autoclave was added 0.539 g (0.588 mmol) of [{RuCl (p-cymene)(R)-segphos}]Cl, then a solution containing 100.0 g (587.5 mmol) of degassed ethyl 2-oxocyclohexanecarboxylate and 400 mL of methylene chloride was added and the mixture was stirred at 40° C. for 22 hours and then at 60° C. for 91 hours under 2 MPa of hydrogen pressure. After cooling, hydrogen was discharged, the solvent was recovered and the residue (123.91 g) was distilled under reduced pressure (80 to 90° C./93.3 Pa) to give 99.37 g of the title compound. The yield was 98%. The resulting product was analyzed and measured by the same manner as in Example 1 and the results were 97.5% ee and 87.5% de.

$^1$H-NMR (200 MHz) δ (CDCl$_3$): 1.3 (t, J=7.1 Hz, 3H), 1.2–1.4 (m, 3H), 1.6–1.8 (m, 3H), 2.0 (m, 2H), 2.2 (m, 1H), 2.8 (d, J=3.2 Hz, 1H), 3.8 (m, 1H), 4.2 (q, J=7.1 Hz, 2H).

Example 4

Synthesis of (R,R)-2-hydroxycyclopentanecarboxylic Hydrazide

To a 200-mL four-necked flask were added 18.47 g (128.1 mmol) of methyl (R,R)-2-hydroxycyclopentanecarboxylate and 75 mL of 2-propanol and stirring was started. Hydrazine monohydrate (12.83 g; 256.2 mmol) was dropped thereinto at 20° C. taking 1 hour and 30 minutes. After the dropping, the mixture was stirred at 85° C. for 15 hours. After the reaction, heating was stopped and the mixture was cooled to room temperature to precipitate the crystals. The crystals were filtered and washed with small amount of 2-propanol. The resulting crystals were dried to give 10.89 g of the title compound. The yield was 59%. Ratio of anti-form to syn-form of the compound was measured by a high-performance liquid chromatography (column: Inertsil ODS-3V) and found that the anti/syn ratio was more than 99/1.

$^1$H-NMR (500 MHz) δ (CD$_3$OD): 1.5–1.6 (m, 1H), 1.7–1.8 (m, 3H), 1.9–2.0 (m, 2H), 2.4 (m, 2H), 4.2–4.3 (m, 1H).

Example 5

Synthesis of (S,S)-2-hydroxycyclopentanecarboxylic Hydrazide

To a 50-mL four-necked flask were added 2.33 g (16.2 mmol) of methyl (S,S)-2-hydroxycyclopentanecarboxylate and 9.3 ml of 2-propanol and stirring was started. Hydrazine monohydrate (1.62 g; (32.3 mmol) was dropped thereinto at 23° C. taking 30 minutes. After the dropping, the mixture was stirred at 85° C. for 15 hours. Followed by, heating was stopped and the mixture was cooled down to room temperature to precipitate the crystals. The crystals were filtered and washed with a small amount of 2-propanol. The resulting crystals were dried to give 1.50 g of the title compound. The yield was 63%. Ratio of anti-form to syn-form of the compound was measured by the same manner as in Example 4 and found that the anti/syn ratio was more than 99/1.

$^1$H-NMR (200 MHz) δ (CD$_3$OD): 1.5–1.6 (m, 1H), 1.7–1.8 (m, 3H), 1.9–2.0 (m, 2H), 2.4 (m, 2H), 4.2–4.3 (m, 1H).

Example 6

Synthesis of (R,R)-2-hydroxycyclohexanecarboxylic Hydrazide

To a one-liter four-necked flask were added 102.5 g (595 mmol) of ethyl (R,R)-2-hydroxycyclohexanecarboxylate and 400 mL of 2-propanol and stirring was started. Hydrazine monohydrate (44.7 g; 893 mmol) was dropped thereinto at 13° C. taking 30 minutes. After the dropping, the mixture was stirred at 80° C. for 9.5 hours. Followed by, heating was stopped and the mixture was cooled to room temperature to precipitate the crystals. The crystals were filtered and washed with a small amount of 2-propanol. The resulting crystals were dried to give 30.10 g of the title compound. The yield was 32%.

$^1$H-NMR (500 MHz) δ (CD$_3$OD): 1.1–1.2 (m, 3H), 1.3 (m, 1H), 1.6–1.7 (m, 3H), 1.8–1.9 (m, 2H), 3.5 (m, 1H), 4.0 (s, 2H), 4.4 (d, J=5 Hz, 1H), 8.7 (s, 1H).

Example 7

Synthesis of (R,R)-2-N-benzyloxycarbonylaminocyclopentanol

To a 50-mL flask were added 0.500 g (3.47 mmol) of (R,R)-2-hydroxycyclopentanecarboxylic hydrazide, 1.5 mL of toluene and 0.5 mL of water and then 0.375 g (3.82 mmol) of concentrated sulfuric acid was dropped thereinto at 3° C. taking 30 minutes. After that, 1 mL (9.71 mmol) of benzyl alcohol was added and 0.5 mL of aqueous solution of 0.263 g (3.82 mmol) of sodium nitrite was dropped thereinto at 3° C. taking 1 hour. After the dropping, the mixture was stirred for 1 hour. An organic layer was collected from the reaction mixture and dropped into a flask containing toluene which was previously heated at 55° C. Followed by, the mixture was stirred for 2 hours. The reaction mixture was extracted and the organic layer was washed with 5 mL of an aqueous saturated sodium hydrogen carbonate. The aqueous layer was extracted with 2 mL of n-butanol, the solvent of the combined organic layer was distilled off and the residue (0.98 g) was purified by silica gel column chromatograph (hexane:ethyl acetate=1:1) to give 0.435 g of the title compound. The yield was 50%.

$^1$H-NMR (200 MHz) δ (CDCl$_3$): 1.2–1.8 (m, 4H), 1.9–2.1 (m, 2H), 3.6–3.7 (m, 2H), 4.0 (m, 1H), 4.9 (br, 1H), 5.1 (s, 2H), 7.3–7.4 (m, 5H).

Example 8

Synthesis of (R,R)-2-N-benzyloxycarbonylaminocyclopentanol

The similar manner to Example 7 except for 35% hydrochloric acid was used instead of concentrated sulfuric acid to obtain the title compound in the yield of 46%. NMR spectrum of the resulting compound was identical with the data for Example 7.

Example 9

Synthesis of (R,R)-2-N-benzyloxycarbonylaminocyclopentanol

The similar manner to Example 7 was carried out except that acetic acid was used instead of concentrated sulfuric acid to obtain the title compound in the yield of 16%. NMR spectrum of the resulting compound was identical with the data for Example 7.

Example 10

Synthesis of (R,R)-2-N-isopropyloxycarbonylaminocyclopentanol

To a 100-mL reaction flask were added 1.00 g (69.36 mmol) of (R,R)-2-hydroxycyclopentanecarboxylic acid hydrazide, 20 mL of toluene and 25 mL of water and then 7.7 mL (76.3 mmol) of 35% hydrochloric acid were dropped thereinto at 3° C. taking 30 minutes. After that, 10 mL (131 mmol) of 2-propanol were added and 10 mL of aqueous solution of 5.26 g (76.3 mmol) of sodium nitrite were dropped thereinto at 2° C. taking 1 hour. After the dropping, the mixture was stirred for 1 hour and an organic layer was taken out from the reaction mixture and dropped, taking 1 hour, into a reaction flask in which toluene previously heated at 55° C. was placed. After the dropping, the mixture was stirred for 2 hours and an organic layer was separated. The aqueous phase was extracted with 10 mL of n-butanol, the solvent of the combined organic layer was distilled off using an evaporator. The residue (4.17 g) was purified by silica gel column chromatography (hexane:ethyl acetate=1:1) to give 5.51 g of the title compound. The yield was 40%.

$^1$H-NMR (200MHz) δ (CDCl$_3$): 1.2 (d, J=6.6 Hz, 6H), 1.3–1.9 (m, 4H), 1.9–2.1 (m, 2H), 3.7 (m, 2H), 3.9–4.0 (m, 1H), 4.9 (br, 1H).

Example 11

Synthesis of (R,R)-2-N-ethoxycarbonylaminocyclopentanol

To a 50-mL reaction flask were added 1.00 g (6.94 mmol) of (R,R)-2-hydroxycyclopentanecarboxylic hydrazide, 2 mL of toluene and 2.5 mL of water and then 0.76 mL (7.63 mmol) of 35% hydrochloric acid were dropped thereinto at 3° C. taking 30 minutes. After that, 2 mL (26.3 mmol) of ethanol were added and 1 mL of aqueous solution of 0.526 g (7.63 mmol) of sodium nitrite was dropped thereinto at 2° C. taking 1 hour. After the dropping, the mixture was stirred for 1 hour and an organic layer was taken out from the reaction mixture and dropped, taking 1 hour, into a flask in which toluene previously heated at 55° C. was placed. After the dropping, the mixture was stirred for 2 hours and an organic layer was separated. The aqueous layer was extracted with 2 mL of n-butanol, the solvent of the combined organic layer was distilled off using an evaporator. The residue (1.12 g) was purified by silica gel column chromatography (hexane:ethyl acetate=1:1) to give 0.46 g of the title compound. The yield was 36%.

$^1$H-NMR (200 MHz) δ (CDCl$_3$): 1.2 (t, J=7 Hz, 3H), 1.3–1.8 (m, 4H), 1.9–2.1 (m, 2H), 3.6–3.7 (m, 2H), 4.0 (m, 1H), 4.8 (br, 1H).

Example 12

Synthesis of (S,S)-2-N-benzyloxycarbonylaminocyclopentanol

To a 50-mL reaction flask were added 1.40 g (9.71 mmol) of (S,S)-2-hydroxycyclopentanecarboxylic hydrazide, 3 mL of toluene and 3.5 mL of water and then 1.1 mL (10.7 mmol) of 35% hydrochloric acid were dropped there into at 0° C. taking 15 minutes. After that, 1.4 mL (13.5 mmol) of benzyl alcohol were added and 1.4 mL of aqueous solution of 0.737 g (10.7 mmol) of sodium nitrite was dropped thereinto at 2° C. taking 1 hour. After the dropping, the mixture was stirred for 1 hour and an organic layer was taken out from the reaction mixture and dropped, taking 1 hour, into a reaction flask in which toluene previously heated at 55° C. was placed. After the dropping, the mixture was stirred for 2 hours and an organic layer was separated. The solvent was distilled off by an evaporator and the residue (2.12 g) was purified by silica gel column chromatography (hexane:ethyl acetate=1:1) to give 0.90 g of the title compound. The yield was 39%.

$^1$H-NMR (200 MHz) δ (CDCl$_3$): 1.2–1.8 (m, 4H), 1.9–2.1 (m, 2H), 3.6–3.7 (m, 2H), 4.0 (m, 1H), 4.9 (br, 1H), 5.1 (s, 2H), 7.3–7.4 (m, 5H).

Example 13

Synthesis of (R,R)-2-N-benzyloxycarbonylaminocyclopentanol

To a 50-mL reaction flask were added 0.500 g (3.47 mmol) of (R,R)-2-hydroxycyclopentanecarboxylic hydrazide, 1.5 mL of toluene and 0.5 mL of water and then 0.398 g (3.82 mmol) of concentrated hydrochloric acid was dropped thereinto at 3° C. taking 30 minutes. After that, 0.5 mL of aqueous solution of 0.263 g (3.82 mmol) of sodium nitrite was dropped thereinto at 3° C. taking 1 hour. After the dropping, the mixture was stirred for 1 hour. An organic layer was taken out from the reaction mixture and dropped, taking 1 hour, into a flask in which benzyl alcohol and toluene previously heated at 55° C. were placed. After the dropping, the mixture was stirred for 2 hours, an organic layer was separated and the organic layer was washed with 5 mL of an aqueous saturated sodium hydrogen carbonate. The solvent was distilled off by an evaporator and the residue was purified by silica gel column chromatography (hexane:ethyl acetate=1:1) to give 0.498 g of the title compound. The yield was 61%.

$^1$H-NMR (200 MHz) δ (CDCl$_3$): 1.2–1.8 (m, 4H), 1.9–2.1 (m, 2H), 3.6–3.7 (m, 2H), 4.0 (m, 1H), 4.9 (br, 1H), 5.1 (s, 2H), 7.3–7.4 (m, 5H).

Example 14

Synthesis of (R,R)-2-aminocyclopentanol

To a 100-mL autoclave were added 5.85 g (24.9 mmol) of (R,R)-2-benzyloxycarbonylaminocyclopentanol and 2.34 g of 5% palladium-carbon, then 29 mL of degassed methanol were added thereto in a nitrogen atmosphere and the mixture was stirred at 50° C. for 3 hours under 2 MPa of hydrogen pressure. The palladium-carbon was filtered off using Celite and the filtrate was concentrated using an evaporator to give 2.60 g of a crude product. The residue was distilled and purified by a Kugelrohr to give 1.42 g of the title compound. The yield was 45%. A % ee of this compound was analyzed by gas chromatography (column: Chiral Dex G-PN) and found to be more than 99% ee.

$^1$H-NMR (500 MHz) δ (CDCl$_3$): 1.2–1.3 (m, 1H), 1.5 (m, 1H), 1.6–1.7 (m, 2H), 1.9–2.0 (m, 2H), 2.3–2.5 (br, 3H), 3.0 (m, 1H), 3.7 (m, 1H).

Example 15

Synthesis of (S,S)-2-aminocyclopentanol

To a 50-mL autoclave were added 0.900 g (3.82 mmol) of (S,S)-2-benzyloxycarbonylaminocyclopentanol and 0.36 g of 5% palladium-carbon, then 4.5 mL of degassed methanol were added thereto in a nitrogen atmosphere and the mixture was stirred at 50° C. for 3 hours under 2 MPa of hydrogen pressure. The palladium-carbon was filtered off using Celite and the filtrate was concentrated using an evaporator to give 0.59 g of a crude product. A % ee of this compound was more than 99% ee.

$^1$H-NMR (200 MHz) δ (CDCl$_3$): 1.2–1.3 (m, 1H), 1.5 (m, 1H), 1.6–1.7 (m, 2H), 1.9–2.0 (m, 2H), 2.3–2.5 (br, 3H), 3.0 (m, 1H), 3.7 (m, 1H).

Example 16

Synthesis of (R,R)-2-aminocyclopentanol Hydrochloride

To a 100-mL autoclave were added 15 g (70.7 mmol) of (R,R)-2-benzyloxycarbonylaminocyclopentanol and 0.3 g of 5% palladium-carbon, then 45 mL of degassed methanol were added thereto in a nitrogen atmosphere and the mixture was stirred at 50° C. for 3 hours under 2 MPa of hydrogen pressure. The palladium-carbon was filtered off using Celite and concentrated hydrochloric acid was added to filtrate until the pH reached 3. The aqueous layer was concentrated to give 7.9 g of the title compound (hydrochloride). The yield was 79.2%.

Example 17

Synthesis of (R,R)-2-aminocyclopentanol Hydrochloride

To a 30-mL flask were added 1 g (4.25 mmol) of (R,R)-2-benzyloxycarbonylaminocyclopentanol, 1.8 g (1.40 mmol) of potassium trimethylsilanolate (KOSiMe$_3$) and 5 mL of tetrahydrofuran followed by stirring at 70° C. for 3 hours. Methanol (5 mL) was added thereto and concentrated hydrochloric acid was added to filtrate until the pH reached 3. After evaporating the solvent, methanol was added thereto, the insoluble matters were filtered off and methanol was evaporated to give 0.40 g of the title compound (hydrochloride). The yield was 70.0%.

As a result of the process for production in accordance with the present invention, it is now possible to produce an optically active amino alcohol having a high optical purity in short steps and in a high yield from an optically active hydroxycarboxylate obtained from an asymmetric hydrogenation of a β-keto ester which is easily available in an industrial scale.

As compared with the conventional producing processes, the process for production in accordance with the present invention does not need troublesome synthetic routes and is an advantageous method which is economically excellent and industrially advantageous.

What is claimed is:

1. A process for the production of an optically active amino alcohol represented by the following formula (I)

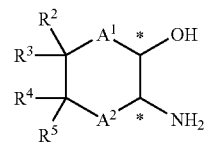

(I)

(wherein, $R^2$, $R^3$, $R^4$ and $R^5$ each independently is a hydrogen atom, a lower alkyl group or an optionally-substituted phenyl group; $R^2$ or $R^3$ may be bonded to $R^4$ or $R^5$ forming a ring together with the adjacent carbon atoms; $A^1$ is —$(CH_2)_m$— while $A^2$ is —$(CH_2)_n$— (where m and n each is an integer of 0 to 3 and m+n is 1 to 3); * is an asymmetric carbon atom where the relative configuration of hydroxyl group to amino group on each of the asymmetric carbons marked * is trans) or a salt thereof, comprising reacting an optically active hydroxycarboxylate represented by the following formula (IV)

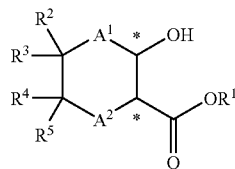

(IV)

(wherein, $R^1$ is an alkyl group having 1 to 6 carbon(s); $R^2$, $R^3$, $R^4$, $R^5$, $A^1$, $A^2$, m, n and * have the same meanings as defined above where the relative configuration of hydroxyl group to alkoxycarbonyl group on each of the asymmetric carbons marked * is trans) with hydrazine to prepare an optically-active hydroxycarboxylic hydrazide compound represented by the following formula (III)

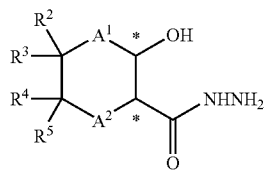

(III)

(wherein, $R^2$, $R^3$, $R^4$, $R^5$, $A^1$, $A^2$, m, n and * have the same meanings as defined above where the relative configuration of hydroxyl group to hydrazinocarbonyl group on each of the asymmetric carbons marked * is trans), then conducting a Curtius reaction in the presence of an alcohol represented by the following formula (VI)

$R^6OH$ (VI)

(wherein, $R^6$ is an alkyl group having 1 to 6 carbon(s) or an optionally-substituted benzyl group) to give an optically active alkoxycarbonylamino alcohol represented by the following formula (II)

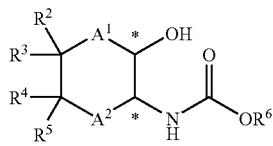

(II)

(wherein, $R^2$, $R^3$, $R^4$, $R^5$, $R^6$, $A^1$, $A^2$, m, n and * have the same meanings as defined above where the relative configuration of hydroxyl group to alkoxycarbonylamino group on each of the asymmetric carbons marked * is trans) and then deprotecting a protective group for the amino group.

2. A process for the production of an optically active alkoxycarbonylamino alcohol represented by the following formula (II)

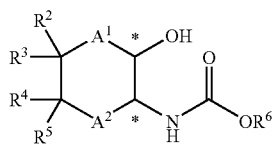

(II)

(wherein, $R^2$, $R^3$, $R^4$ and $R^5$ each independently is a hydrogen atom, a lower alkyl group or an optionally-substituted phenyl group; $R^2$ or $R^3$ may be bonded to $R^4$ or $R^5$ forming a ring together with the adjacent carbon atoms; $R^6$ is an alkyl group having 1 to 6 carbon(s) or an optionally-substituted benzyl group; $A^1$ is —$(CH_2)_m$— while $A^2$ is —$(CH_2)_n$— (where m and n each is an integer of 0 to 3 and m+n is 1 to 3); * is an asymmetric carbon atom where the relative configuration of hydroxyl group to alkoxycarbonylamino group on each of asymmetric carbons marked * is trans), comprising reacting an optically active hydroxycarboxylate represented by the following formula (IV)

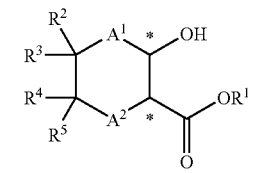

(IV)

(wherein, $R^1$ is an alkyl group having 1 to 6 carbon(s); $R^2$, $R^3$, $R^4$, $R^5$, $A^1$, $A^2$, m, n and * have the same meanings as defined above where the relative configuration of hydroxyl group to alkoxycarbonyl group on each of the asymmetric carbons marked* is trans) with hydrazine to prepare an optically-active hydroxycarboxylic hydrazide compound represented by the following formula (III)

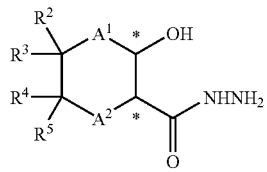

(III)

(wherein, $R^2$ $R^3$, $R^4$ $R^5$, $A^1$, $A^2$, m, n and * have the same meanings as defined above where the relative configuration of hydroxyl group to hydrazinocarbonyl group on each of the asymmetric carbons marked * is trans) and conducting a Curtius reaction in the presence of an alcohol represented by the following formula (VI)

$R^6OH$  (VI)

(wherein, $R^6$ is an alkyl group having 1 to 6 carbon(s) or an optionally-substituted benzyl group).

3. The process according to claim 1 or 2, wherein the optically active hydroxycarboxylate represented by the following formula (IV)

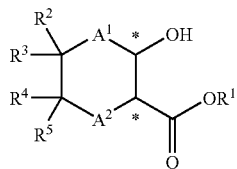

(IV)

(wherein, $R^1$, $R^2$ $R^3$, $R^4$, $R^5$, $A^1$, $A^2$, m, n and * have the same meanings as defined above where the relative configuration of hydroxyl group to alkoxycarbonyl group on each of the asymmetric carbons marked * is trans) is a product prepared by subjecting a β-keto ester represented by the following formula (V)

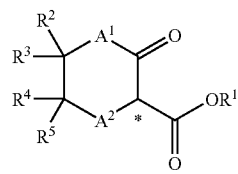

(V)

(wherein, $R^1$, $R^2$ $R^3$, $R^4$, $R^5$, $A^1$, $A^2$, m and n have the same meanings as defined above) to an asymmetric hydrogenation in the presence of a ruthenium complex including an optically active phosphine compound as a ligand.

4. The process according to claim 1 or 2, wherein $R^6$ is an optionally substituted benzyl group.

5. The process according to claim 1 or 2, wherein $R^6$ is a benzyl group.

6. The process of claim 3 wherein $R^6$ is an optionally substituted benzyl group.

7. The process of claim 3 wherein $R^6$ is a benzyl group.

* * * * *